United States Patent [19]
Dunkak et al.

[11] Patent Number: 5,939,295
[45] Date of Patent: Aug. 17, 1999

[54] PRODUCTION OF TRYPTOPHAN BY MICROORGANISMS

[75] Inventors: Mark S. Dunkak, Decatur; Richard D. Dancey, Mt. Zion; Thomas W. McMullin, Bettendorf; Paul D. Hanke, Urbana, all of Ill.

[73] Assignee: Archer Daniels Midland Company, Decatur, Ill.

[21] Appl. No.: 08/627,696

[22] Filed: Mar. 29, 1996

[51] Int. Cl.$^6$ .............................. C12P 13/22; C12N 1/20; C12N 15/00

[52] U.S. Cl. .................. 435/108; 435/252.3; 435/252.33; 435/320.1

[58] Field of Search ................................ 435/108, 252.3, 435/252.33, 320.1

[56] References Cited

FOREIGN PATENT DOCUMENTS

87/01130  2/1987  WIPO .

OTHER PUBLICATIONS

Mascarenhas et al. App. Env. Microbiol. 57 : 2995, 1991.

*Primary Examiner*—Robert A. Wax
*Assistant Examiner*—Tekchand Saidha
*Attorney, Agent, or Firm*—Laff, Whitesel, Conte & Saret, Ltd.

[57] ABSTRACT

An improved recombinant DNA plasmid composed of a DNA vector and other DNA fragments containing the tryptophan operon from *E. coli*, the aroG gene from *E. coli* and the serA gene from *E. coli* is shown. The plasmid is transformed into a microorganism belonging to *Escherichia coli*, and the microorganisms are cultured in a medium and the L-tryptophan accumulated in the culture is recovered.

11 Claims, 10 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: YES (iv) ANTI-SENSE: NO (vi) ORIGINAL SOURCE:
      (A) ORGANISM: Escherichia coli (vii) IMMEDIATE SOURCE:
      (B) CLONE: UV5-1A (xi) SEQUENCE DESCRIPTION: SEQ ID NO:1:

TAGGCGTATC AGGAGGCCCT          20

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: YES (iv) ANTI-SENSE: NO (vi) ORIGINAL SOURCE:
        (A) ORGANISM: Escherichia coli (vii) IMMEDIATE SOURCE:
        (B) CLONE: UV5-2

(xi) SEQUENCE DESCRIPTION: SEQ ID NO:2:

TGAATCGGAA CTCTCTGAAC CG                                   22

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: YES (iv) ANTI-SENSE: NO (vi) ORIGINAL SOURCE:
        (A) ORGANISM: Escherichia coli (vii) IMMEDIATE SOURCE:
        (B) CLONE: UV5-3C (xi) SEQUENCE DESCRIPTION: SEQ ID NO:3:

CATGATCTCG GCGTATATCG                                      20

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: YES (iv) ANTI-SENSE: NO (vi) ORIGINAL SOURCE:
        (A) ORGANISM: Escherichia coli (vii) IMMEDIATE SOURCE:
        (B) CLONE: PRIMER 1

(xi) SEQUENCE DESCRIPTION: SEQ ID NO:4:

CGAATTCTGT TGACAATTAA TCATCGGCTC GTATAATGTG                40

(2) INFORMATION FOR SEQ ID NO:5:

(i) SEQUENCE CHARACTERISTICS:
        (A) LENGTH: 20 base pairs

```
      (B) TYPE: nucleic acid
      (C) STRANDEDNESS: single
      (D) TOPOLOGY: linear (ii) MOLECULE TYPE: other nucleic acid (iii) HYPOTHETICAL: YES (iv) ANTI-SENSE: NO (vi) ORIGINAL SOURCE:
       (A) ORGANISM: Escherichia coli (vii) IMMEDIATE SOURCE:
        (B) CLONE: PRIMER 2

(xi) SEQUENCE DESCRIPTION: SEQ ID NO:5:

CATGATCTCG GCGTATATCG                                         20
```

PRODUCTION OF TRYPTOPHAN BY MICROORGANISMS

The invention relates to a microorganism, *Escherichia coli* K-12, and more particularly to transforming the microorganism by a recombinant DNA plasmid.

BACKGROUND OF THE INVENTION

The fermentative production of tryptophan by microorganisms from inexpensive carbohydrates is highly desirable. The production of tryptophan by using artificially mutated microorganisms has been known for some time. Classically mutated microbes for tryptophan production include Brevibacterium (described in U.S. Pat. No. 3,700,536), Corynebacterium (ATCC 21851), *Bacillus subtilis* (described in U.S. Pat. No. 4,363,875), and Enterobacter (described in U.S. Pat. No. 4,439,627).

The use of recombinant DNA technology for the construction of microorganisms for production of tryptophan has been described. These descriptions include Corynebacterium or Brevibacterium (described in U.S. Pat. No. 5,447,857) and Bacillus (described in U.S. Pat. No. 4,588,687). The use of recombinant DNA techniques for the construction of *E. coli* strains for tryptophan production has also been described in U.S. Pat. No. 4,371,614. In this patent, the maximum production of tryptophan is about 230 ppm or 230 mg/l. However, this amount of tryptophan production is too low for a commercially feasible production strain.

Work to improve tryptophan production was described in (WO 87/01130) and in *Applied and Environmental Microbiology* (1991) 57: 2995–2999. These documents describe a two plasmid system developed by Stauffer Chemical Co. containing a feedback resistant AS gene (trpE) isolated from *Serratia marcessens* and a feedback resistant DS gene (aroG) from *E. coli*. These plasmids also contained the rest of the trp operon trpDCDA from *E. coli* coding for the APRT, PRAI, InGPS and TS enzymes respectively. One of the plasmids also contained the serA gene used to maintain the plasmid. It is believed that the overexpression of the serA gene product may increase serine concentration in the cell. Serine is one of the precursors of tryptophan. These documents also describe the use of the lacUV5 promoter to control the DS gene and the trpDCBA genes. The maximum production of tryptophan disclosed in this work is about 2400 ppm or 2.4 g/l.

The lacUV5 promoter was used by Stauffer to eliminate the natural regulation of the trp operon and aroG genes. The lacUV5 promoter is a mutated form of the lac promoter that was selected for relief of catabolite repression. The lac promoter is composed of two regions: the RNA polymerase binding site, which is composed of –10 and –35 regions, and the CAP binding site located at about the –60 region from the transcription start site. The CAP site binds the catabolite activator protein (CAP) that is responsible for activating a transcription of the lac operon when there is no glucose present. When glucose is present, CAP does not bind and transcription is not activated. There is a very low transcription from the lac promoter in the presence of glucose. This phenomenon is known as catabolite repression.

In the –10 region, the lacUV5 promoter is changed from the lac promoter by a mutation from GT to AA. This mutation in the lac promoter was found by selecting for a strain that no longer had catabolite repression of the lac operon. The reduction in catabolite repression appears to result from a better binding of the RNA polymerase to the lacUV5 promoter without the need for CAP.

The tac promoter is a combination of the lacUV5 promoter and the trp promoter using the –10 region from the lacUV5 promoter and the –35 region from the trp promoter which makes a better RNA polymerase binding site. The tac promoter no longer contains the CAP binding site, thus eliminating any catabolite repression. Under certain conditions, the tac promoter is about seven times stronger than the lacUV5 promoter. Both the lacUV5 and tac promoters still contain the lac operator region that binds the lacI gene product, the lac repressor, so both of these promoters still respond to an induction by β-galactosides such as lactose and isopropyl-β-D-thiogalactoside (IPTG).

Further development of the Stauffer two plasmid system and the bacterial host resulted in a one plasmid system that contains a trpEDCBA operon from *E. coli* including an *E. coli* feedback resistant AS gene, replacing the *S. marcessens* AS gene. The trp operon has the attenuator and promoter region removed and is controlled by the tandem lacUV5 promoter described in the Stauffer work. This plasmid, pBE7, also contains the feedback resistant aroG gene coding for the DS enzyme from one of the Stauffer plasmids under the control of the tandem lacUV5 promoters. Also contained on the pBE7 plasmid are the serA and lacI genes from the Stauffer plasmids. The invention uses various plasmids developed from the plasmid pBE7 illustrated in FIG. 1.

The host strain (JB102) was also developed from Stauffer's host strain. The host strain was developed in several steps from the bacterial strain B1238 having the genotype [W3110 F' Δ(lacU169), Δ(gal-bio), (trp-lac)) W205 (trp-61-intc-226)], as described by Benedik et al., Gene, 19:303–311 (1982). This strain B1238 was further developed into strain C534 by the Stauffer Chemical Company as described in WO 87/01130. Strain C534 was further developed by Genencor International by a P1 transduction using a lysate of W3110 and transducing C534 to the genotype trp+, lac–. The resulting strain, PB103, was then transduced with a P1 lysate from the strain JC158 described in Genetics (1963) 48:105–120, which is serA, and a strain was selected that was serA. This strain is JB102 and has the genotype [lacU169, tna, serA, anthranilate resistant].

The Genencor strain (JB102/pBE7) produces about 35 g/l tryptophan in fermenters.

SUMMARY OF THE INVENTION

In keeping with an aspect of the invention, the *Escherichia coli* K-12 has a recombinant plasmid DNA containing genes encoding the following enzymes for the synthesis of L-tryptophan: aroG encodes 3-deoxy-D-arabino-heptulosonate-7-phosphate synthase (DS), trpE encodes anthranilate synthase (AS), trpD encodes anthranilate phosphoribosyl transferase (APRT), trpC encodes both N-5'-phosphoribosyl anthranilate isomerase (PRAI) and indole-3-glycerol phosphate synthase (InGPS), and trpBA encodes tryptophan synthase (TS), enabling tryptophan to accumulate in the fermentation medium and recovery of tryptophan from the medium. According to the present invention, L-tryptophan production is enhanced by using a strain of *E. coli* which has a recombinant DNA plasmid containing the genetic information from *E. coli* for the synthesis of the following enzymes: DS, AS, PRT, PRAI, InGPS, and TS. These genes are regulated by the tac promoter. The lacI gene product is inducible by isopropyl-β-D-thiogalactoside (IPTG) or lactose or other β-galactoside analogs. The tac promoter is also on the plasmid and is used to regulate the synthesis of the enzyme under the control of the tac promoter. Also contained on the plasmid is the serA gene which helps to maintain the plasmid in a serA deficient host strain and may help overproduce serine which is needed for tryptophan biosynthesis. The *E. coli* host is defective in tryptophanase. Transformants which are selected have no serine requirement.

DESCRIPTION OF THE PREFERRED EMBODIMENTS

The present invention provides *E. coli* strains capable of producing L-tryptophan by fermentation. The preparation of the plasmids may be described as follows. Essentially, the trp operon from pBE7 is transferred to a vector derived from pBR322. The tandem lacUV5 promoter of pBE7 is replaced by a promoter related to the commercially available tac promoter. Also included on the plasmid is the aroG gene controlled by the tac promoter and the serA gene and the lacI gene. Unexpectedly, a higher rate of tryptophan production is obtained, even without inducing the tac promoter with the lactose analog IPTG.

1. Preparation of plasmids containing the trp operon from plasmid pBE7.

Figure 1:
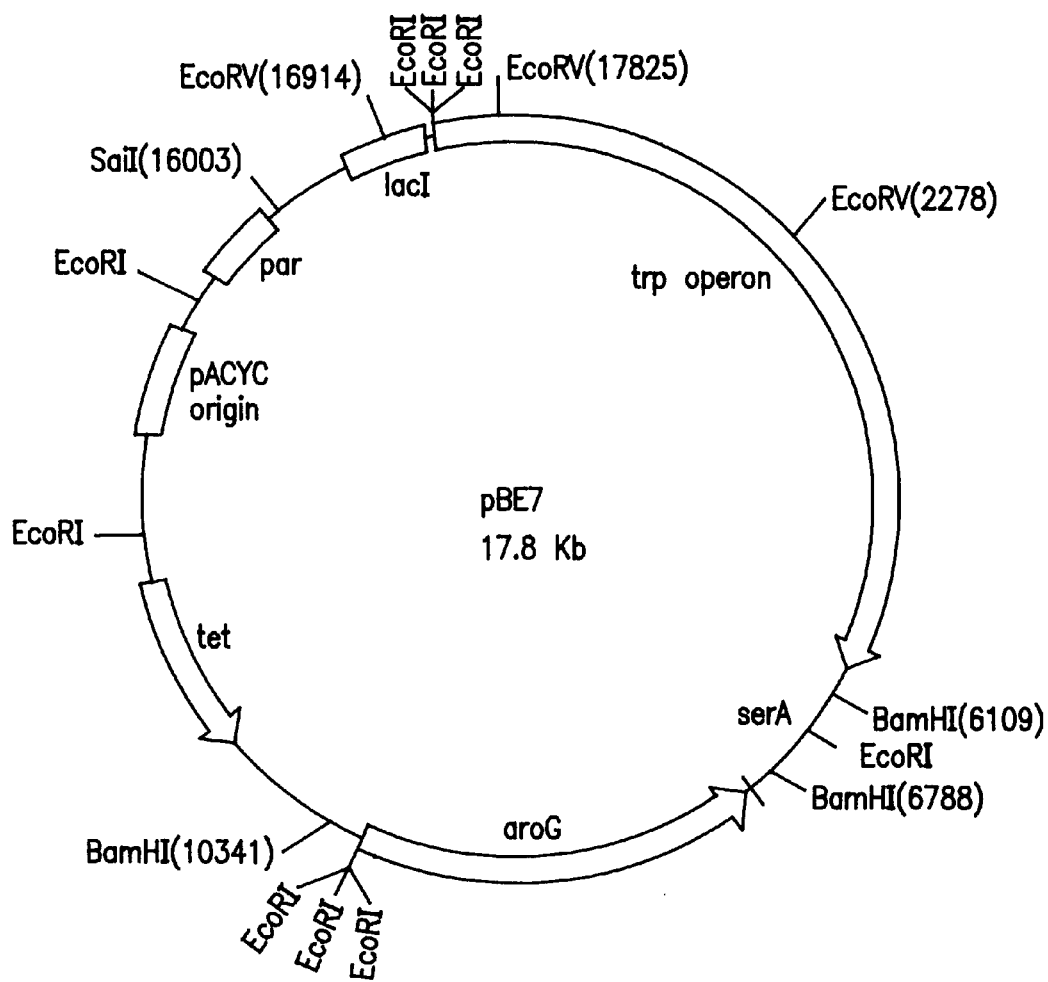
FIG. 1 shows the plasmid pBE7. Only relevant restriction endonuclease sites are shown.
Figure 3:
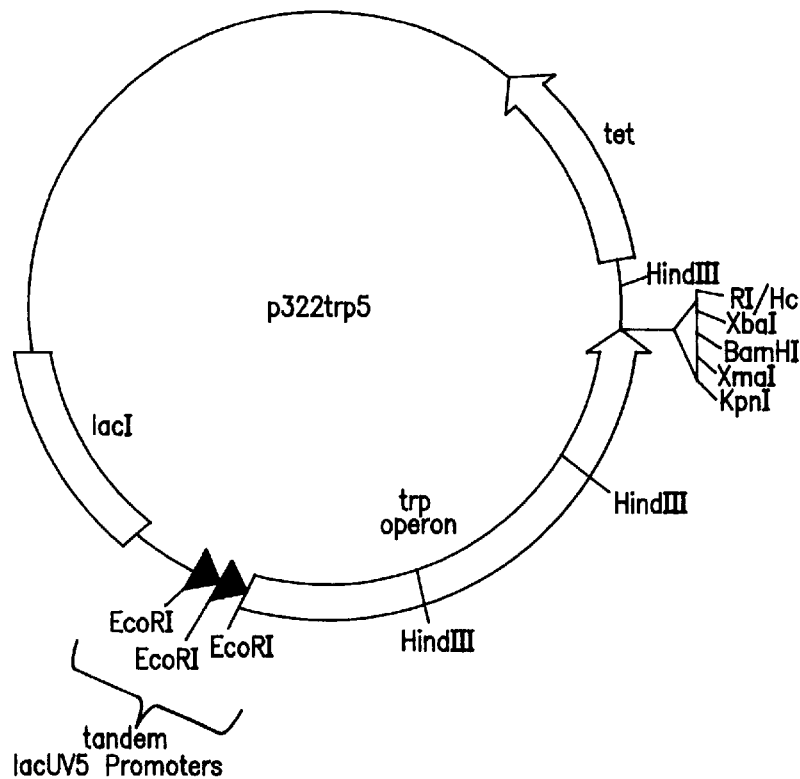
FIG. 3 shows the constructs p322trp5 and p322trp6.
Figure 3:
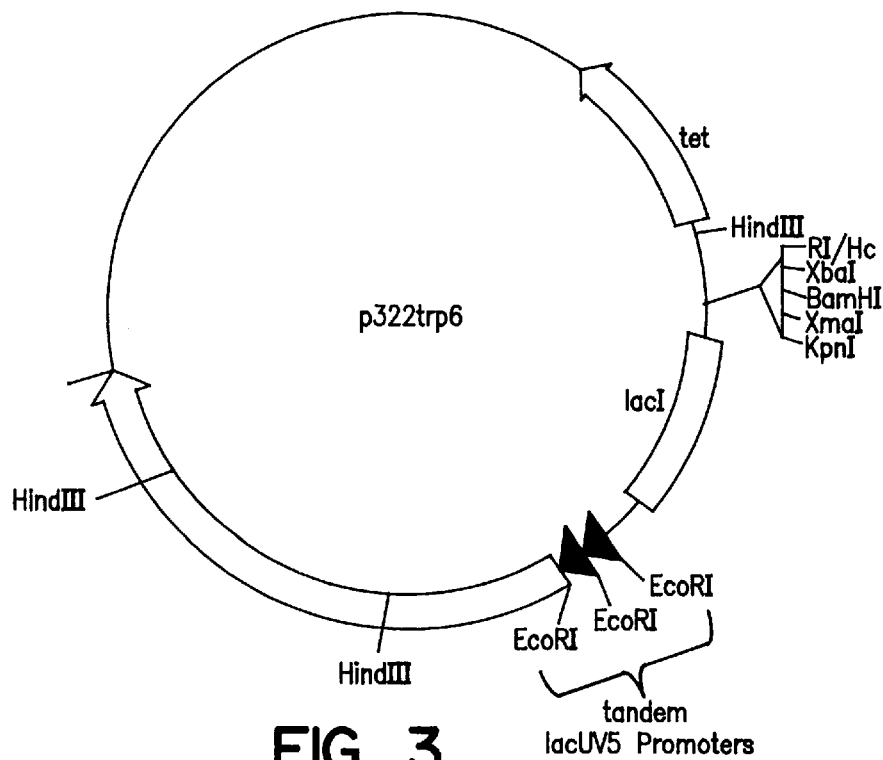

The plasmid pBE7, shown in FIG. 1, is digested with the commercially available restriction enzymes BamHI and SalI to form BamHI-SalI DNA fragments. One BamHI-SalI fragment from pBE7 contains the trp operon which is controlled by tandem lacUV5 promoters and the lacI gene. This BamHI-SalI fragment is cloned into BamHI-SalI sites of the commercially available plasmid Bluescript KS- to form a plasmid referred to as pBStrp. The plasmid, pBStrp, is then digested with the restriction enzymes SphI and BamHI. The ends of the DNA fragments resulting from the digestion were made blunt using T4 DNA polymerase. KpnI linkers were added to the blunt-ended fragments, which were then digested with the restriction enzyme KpnI and ligated into the KpnI restriction enzyme site of the commercially available plasmid, pUC19, to form a plasmid designated as pUCtrp. The KpnI fragment containing the trp operon and lacI gene is then cloned into a vector called p322KX (which is described below) to form plasmids called p322trp5 and p322trp6, as best seen in FIG. 3, which have the KpnI fragment cloned in opposite orientation. Most cloning steps used *E. coli* competent DH5α cells purchased commercially for transformation, followed by appropriate selection.

Figure 2:
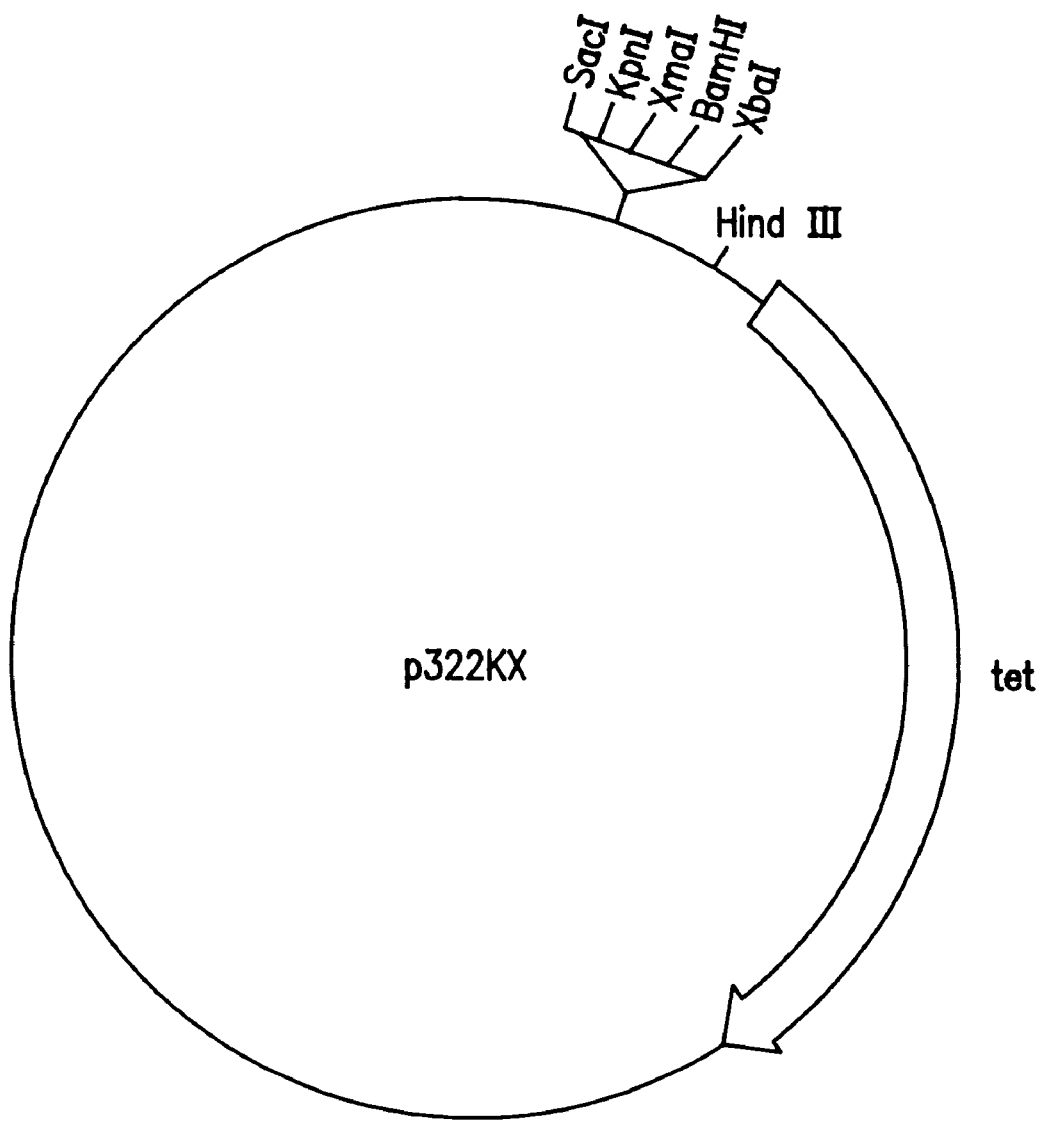
FIG. 2 shows the plasmid p322KX, which is derived from pBR322.

The vector or plasmid p322KX, shown in FIG. 2, was derived from the commercially available plasmid pBR322. Plasmid p322KX (FIG. 2) contains all of pBR322 from the EcoRI site (base pair 4361) of pBR322 to the DraI site (base pair 3230) of pBR322. At the EcoRI site is added a partial pUC19 polylinker containing the restriction sites XbaI, BamHI, XmaI, KpnI and SacI. The EcoRI sites have been destroyed. Thus, p322KX contains no EcoRI sites. This plasmid also has the entire amp gene of pBR322 removed and is tetracycline resistant.

The constructs shown in FIG. 3, p322trp5 and p322trp6, have the trp operon controlled by tandem lacUV5 promoters. In order to facilitate changing promoters, "promoterless constructs" derived from p322trp5 and p322trp6 were made by digesting the plasmids p322trp5 or p322trp6 with the restriction enzyme EcoRI to release the promoter from the rest of the plasmid. The digested plasmid is religated with DNA ligase. Promoterless plasmids were selected by choosing constructs lacking the 200 bp EcoRI lacUV5 promoter fragment. These promoterless constructs are designated p322trp5ΔlacUV5 and p322trp6ΔlacUV5 and best seen in FIG. 4.

Figure 4:
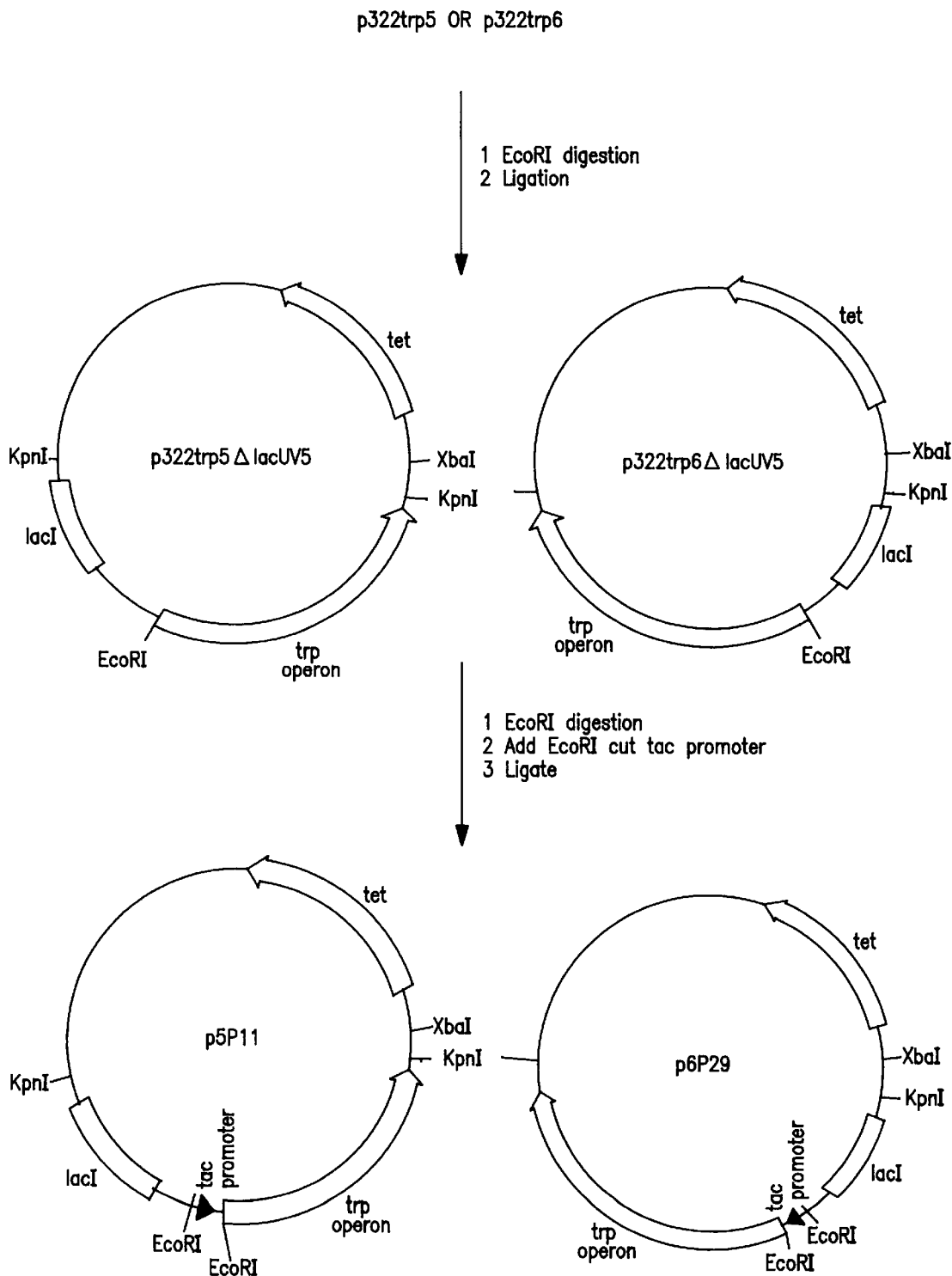
FIG. 4 shows the construction of p5P11 and p6P29.

An EcoRI cassette containing the tac promoter was made by polymerase chain reaction ("PCR") using standard conditions using p322trp5 plasmid as a template DNA and the following primers: 5' CGAATTCTGTTGACAATTAAT-CATCGGCTCGTATAATGTG3' (primer 1) SEQ ID NO 4 and 5' CATGATCTCGGCGTATATCG3' (primer 2) SEQ ID NO 5. Primer 1 is homologous to sequences in the lacUV5 promoter, while primer 2 is homologous to sequences in the trp operon. Thus, this will give two PCR products of about 100 base pairs ("bp") or 300 bp depending on which of the tandem lacUV5 promoters primer 1 hybridizes to. The 100 bp PCR product was digested with EcoRI and the 100 bp tac promoter fragment was isolated. This 100 bp tac promoter is similar to the commercially available tac promoter. As seen in FIG. 4, the 100 bp tac promoter fragment is then cloned into the EcoRI restriction enzyme site of the promoterless constructs, p322trp5ΔlacUV5 and p322trp6ΔlacUV5, which were derived from p322trp5 and p322trp6. The two new plasmids, which have the trp operon controlled by the 100 bp tac promoter, were called p5P11 and p6P29 as seen in FIG. 4. These constructs have the trp operon under the control of the tac promoter.

2. Preparation of an XbaI cassette containing the aroG and serA genes.

Figure 5:
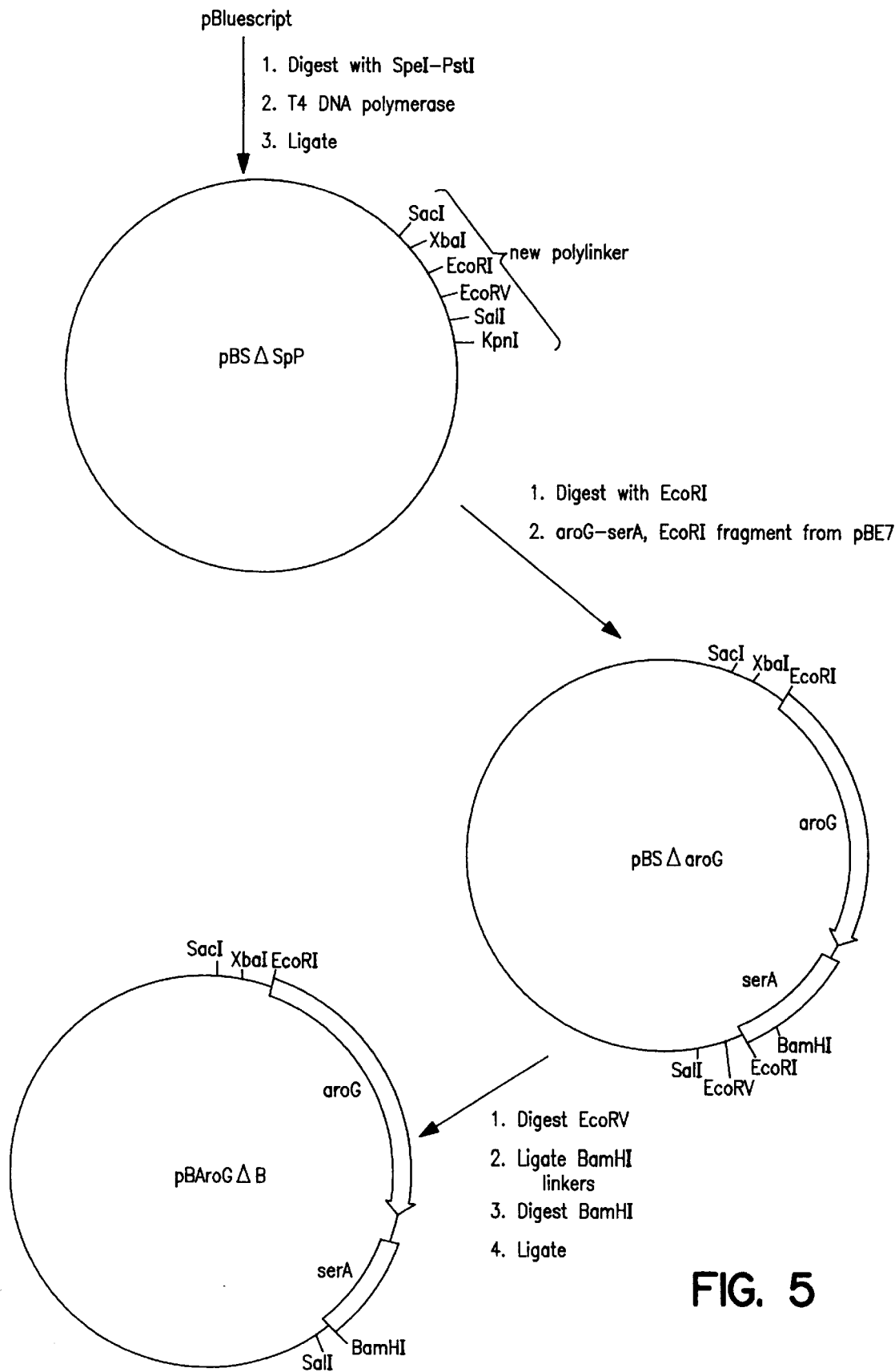
FIG. 5 shows the construction of plasmid pBaroGΔB which contains a promoterless aroG and the 5' end of the serA gene from pBE7.
Figure 6:
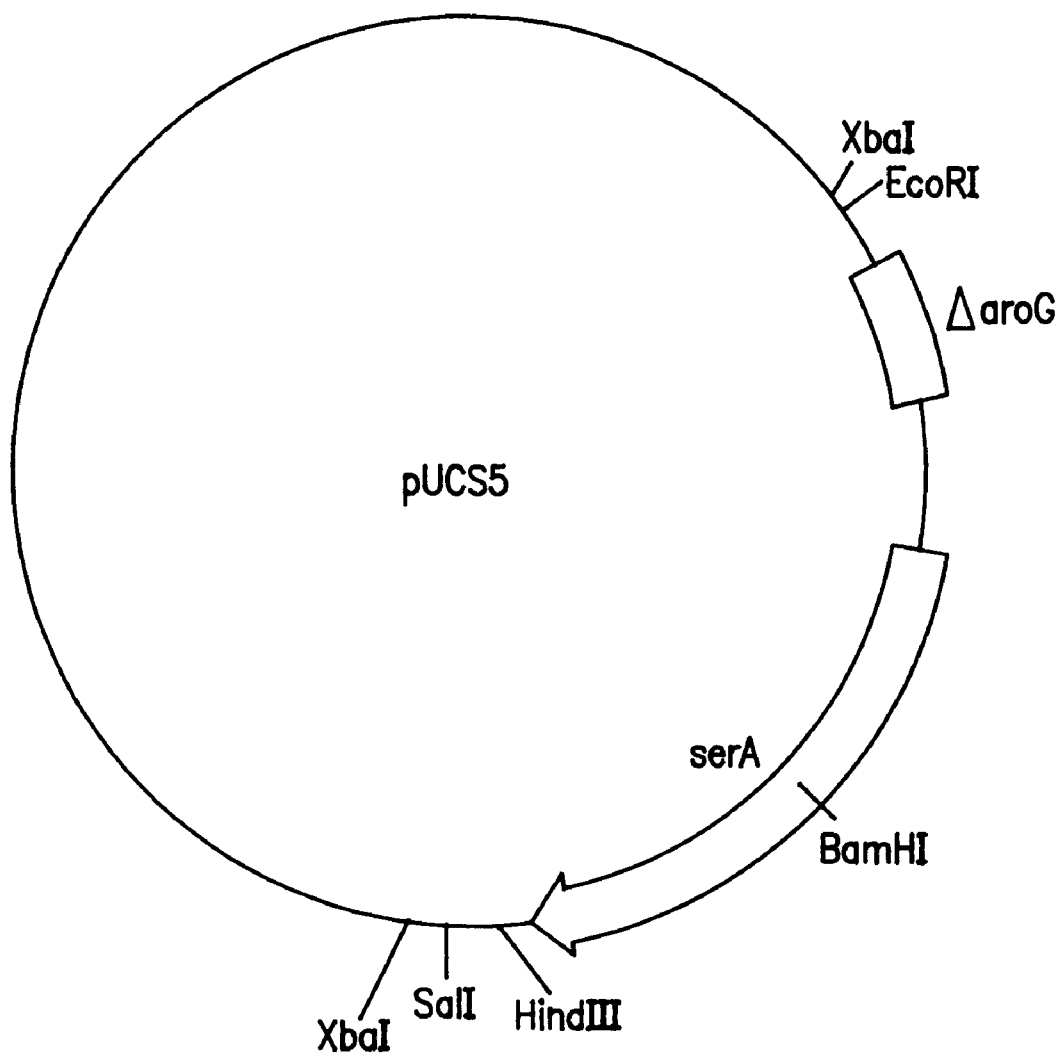
FIG. 6 shows the plasmid pUCS5 which contains the entire serA gene and the 3' end of aroG from pBE7.

A cassette was constructed with XbaI restriction enzyme sites on the ends and carrying an aroG gene controlled by the tac promoter and a serA gene controlled by its natural promoter. First, the commercially available plasmid Bluescript SK- was digested with the restriction enzymes SpeI and PstI to form SpeI-PstI fragments. The ends of the fragments were blunted with T4 DNA polymerase and ligated to eliminate the BamHI site in Bluescript, forming the plasmid or vector pBSΔSpP. To this vector, pBSΔSpP, the EcoRI restriction enzyme fragment from pBE7 containing the aroG gene and a partial 5' serA gene is cloned, forming the plasmid pBSΔAroG as seen in FIG. 5.

This plasmid, pBSΔAroG, was cut with the restriction enzyme EcoRV which cuts in the Bluescript SK⁻polylinker.

Figure 7:
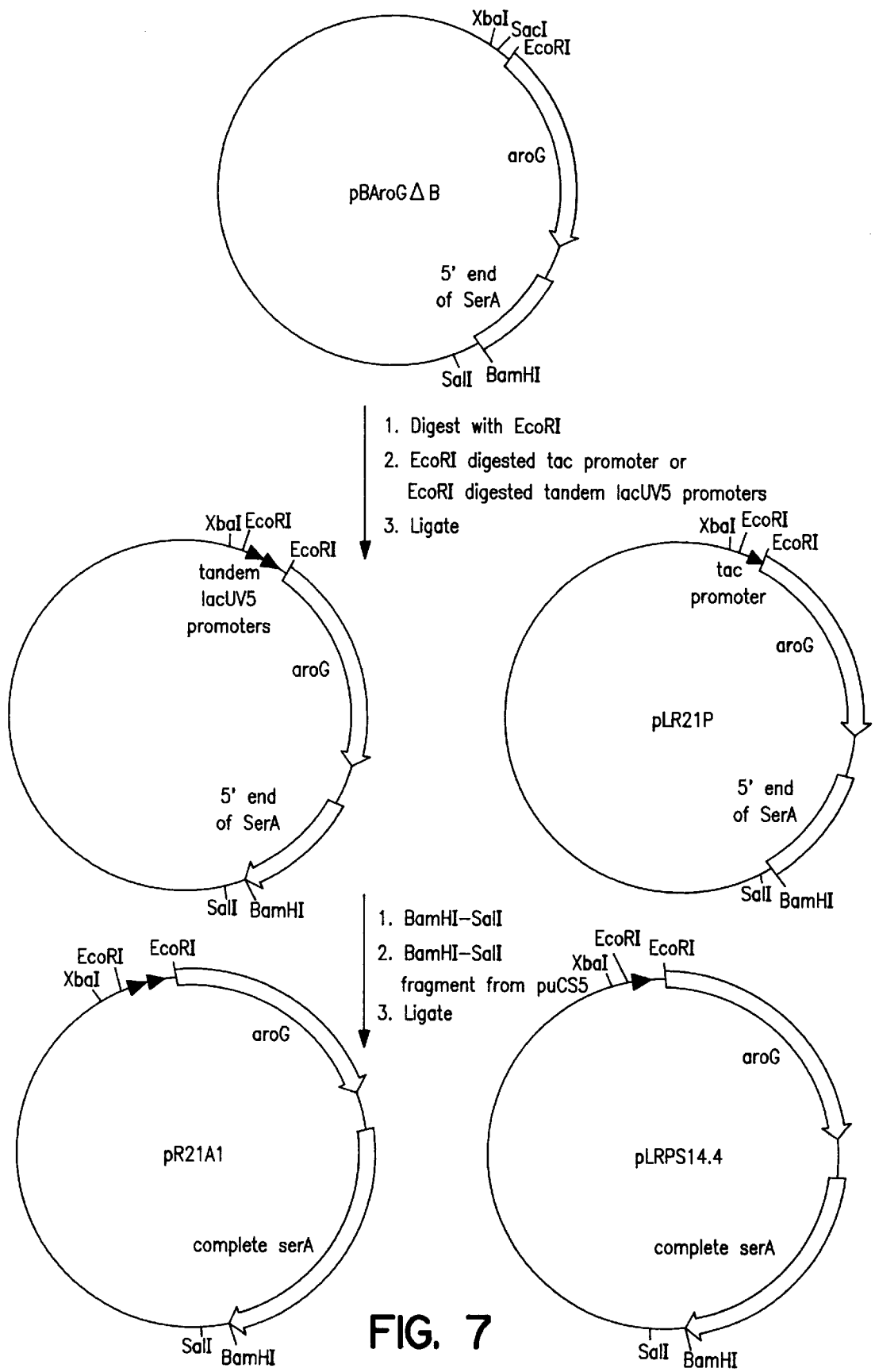
FIG. 7 shows the derivation of pR21A1, which contains the aroG gene controlled by tandem lacUV5 promoters and pLRPS14.4 which contains the aroG gene controlled by a single tac promoter. They also both contain the serA gene.

BamHI DNA linkers were ligated to the resulting EcoRV ends. The ligation was then digested with the restriction enzyme BamHI and re-ligated, which eliminated the EcoRI site in the serA gene. The plasmid pBAroGΔB (FIG. 5) contains the EcoRI-BamHI fragment from pBE7 which contains a promoterless aroG and the 5' end of serA. The EcoRI fragment containing the tac promoter made by PCR as described previously was then added at the only remaining EcoRI site upstream of the aroG gene. This gives an aroG gene controlled by the tac promoter in the plasmid referred to as pLR21P as best seen in FIG. 7.

Plasmid pUCS5 contains the entire serA gene and the 3' end of the aroG gene cloned on an XbaI fragment in pUC19.

The plasmid pUCS5 (FIG. 8) is digested with the restriction enzymes BamHI and SalI to release a DNA fragment containing the 3' end of the serA gene. The BamHI-SalI fragment containing the 3' end of the serA gene is isolated from pUCS5 and added to the plasmid pLR21P digested with BamHI and SalI to recreate the serA gene. As seen in FIG. 7, this construct is designated pLRPS14.4 and contains a feedback resistant aroG gene controlled by the tac promoter as described above and the serA gene.

Similarly, a construct is made using tandem lacUV5 promoters at the EcoRI site instead of the tac promoter. This plasmid is called pR21A1 and contains the feedback resistant aroG gene controlled by tandem lacUV5 promoters and the serA gene on a XbaI fragment, as best seen in FIG. 7.

Figure 8:
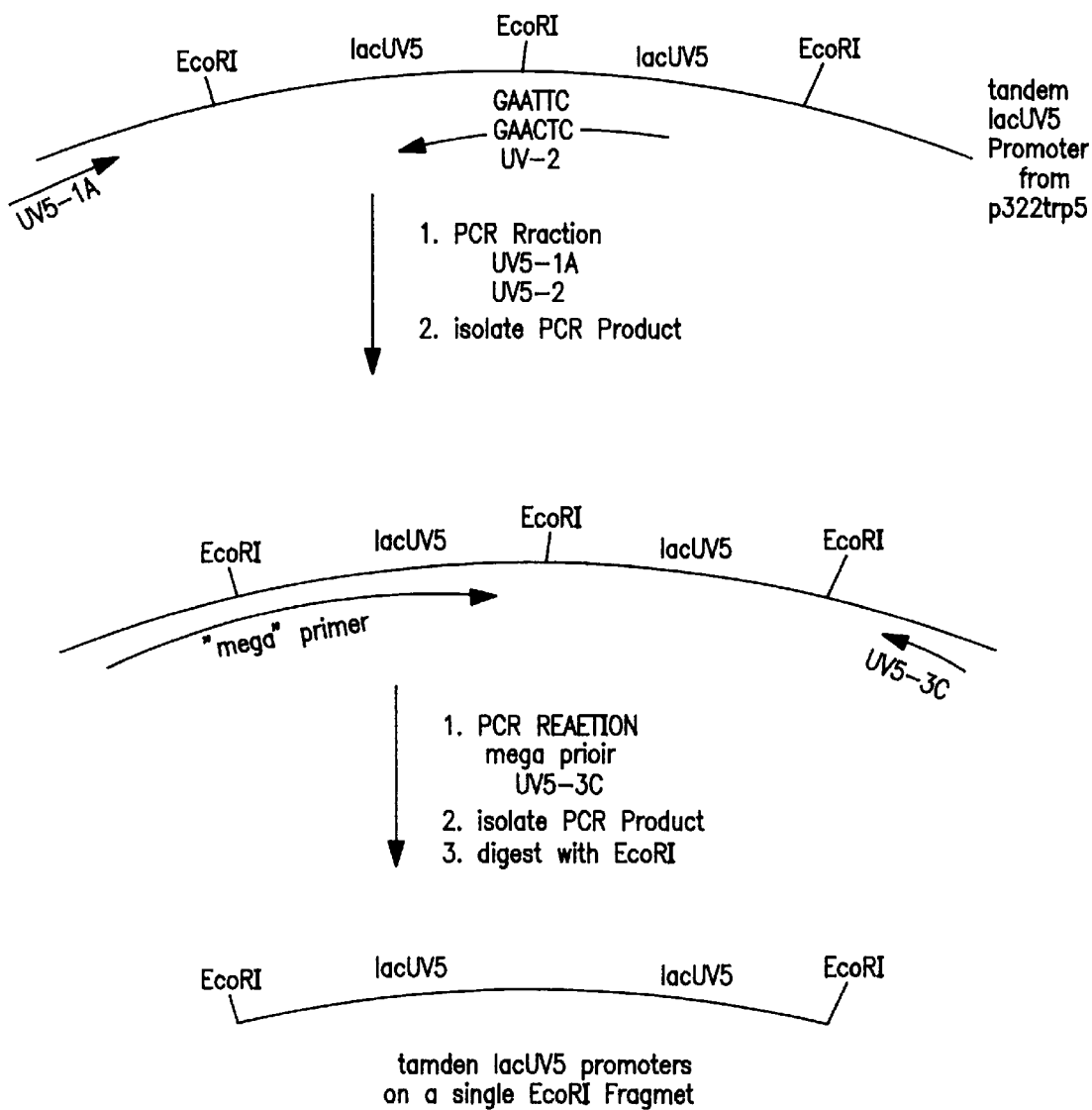
FIG. 8 shows the construction of an EcoRI fragment containing tandem lacUV5 promoters, using mutagenic PCR.

A tandem lacUV5 promoter on a single EcoRI fragment was constructed using PCR, as seen in FIG. 8. This was done by using p322trp5 plasmid as a template DNA, a mutagenic primer UV5-2 SEQ ID NO 2 having the sequence 5'TGAATCGGAACTCTCTGAACCG3', and a primer UV5-1A SEQ ID NO 1 having the sequence 5'TAGGCGTATCAGGAGGCCCT3'. This will give a PCR product where the EcoRI site between the two lacUV5 promoters has been changed so that the restriction enzyme EcoRI will no longer digest the DNA at this site. The PCR product of this PCR reaction is isolated and used as a "mega" primer along with primer UV5-3C SEQ ID NO 3 having the sequence 5'CATGATCTCGGCGTATATCG3' in a second PCR reaction. This second PCR reaction results in a product that contains two tandem lacUV5 promoters but does not have an internal EcoRI site and can be cloned directly as a single EcoRI fragment. The tandem lacUV5 promoters were used in the construction of PR21A1.

3. Construction of tryptophan production plasmids.

Figure 9:
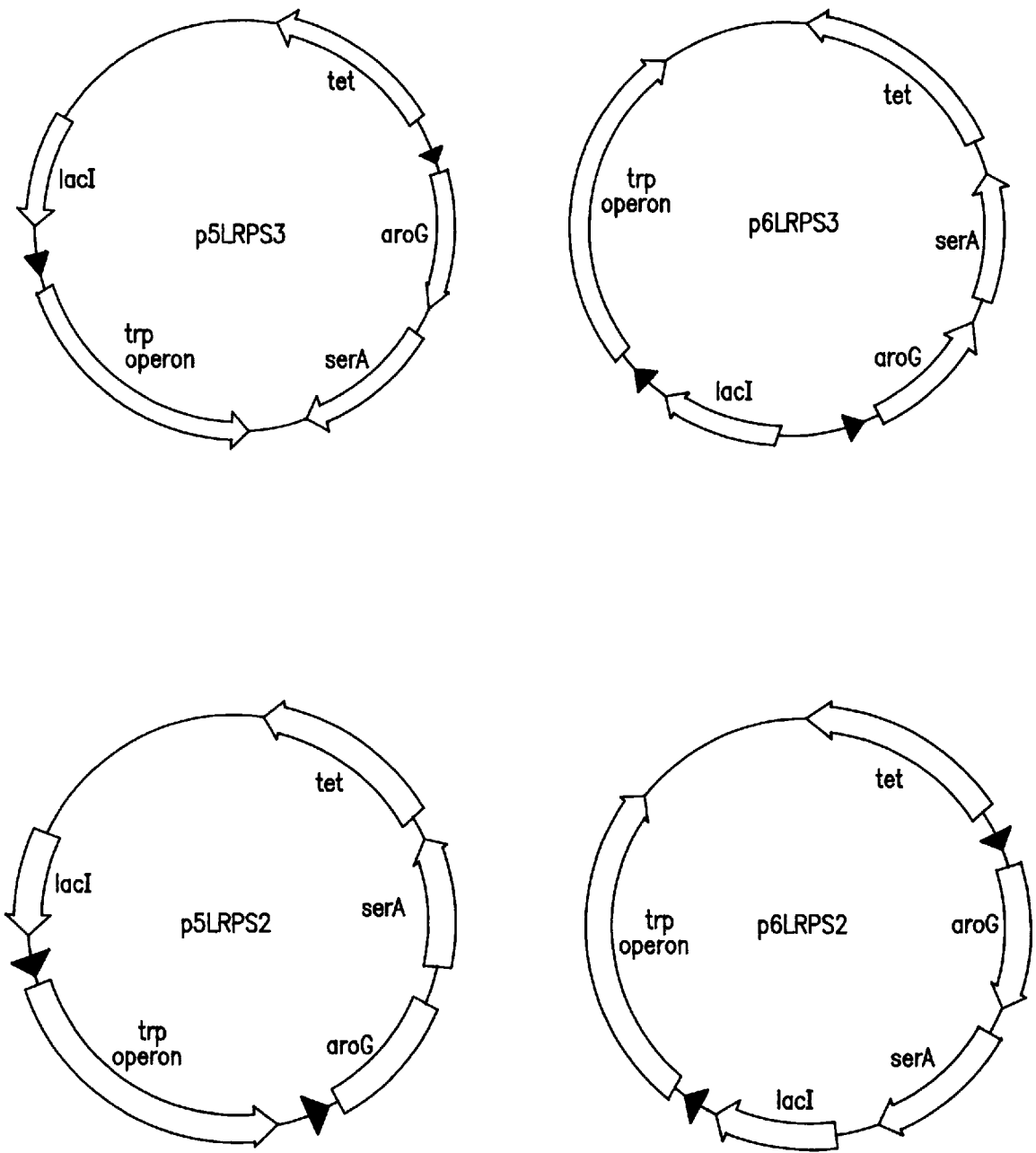
FIG. 9 shows four final tryptophan production plasmids that have tac promoters controlling both the trp operon and the aroG gene.

The plasmids illustrated in FIGS. 3 and 4, which contain the tryptophan operon and lacI, are p322trp5, p322trp6, p5P11 or p6P29, are digested with the restriction enzyme XbaI. Either pLRPS14.4 or pR21A1, illustrated in FIG. 7, is also digested with XbaI and the resulting XbaI fragment containing serA and aroG is ligated into these tryptophan-operon-containing plasmids. This produces a series of different plasmids with different orientations of the trp operon lacI cassette and the aroG serA cassette. FIG. 9 shows a set of the 4 possible tryptophan production plasmids with tac promoters controlling both the trp operon and the aroG gene. These plasmids are referred to as p5LRPS3, p6LRPS3, p5LRPS2, and p6LRPS.

Figure 10:
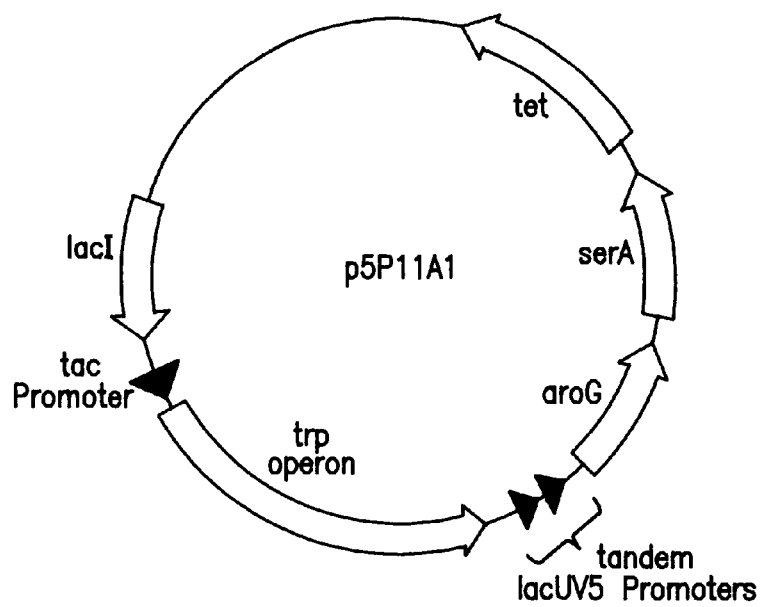
FIG. 10 shows two other tryptophan production plasmids. Plasmid p5P11A1 has a tac promoter controlling the trp operon and tandem lacUV5 promoters controlling the aroG gene. Plasmid p5R21A1 has tandem lacUV5 promoters controlling both the trp operon and the aroG gene.
Figure 10:
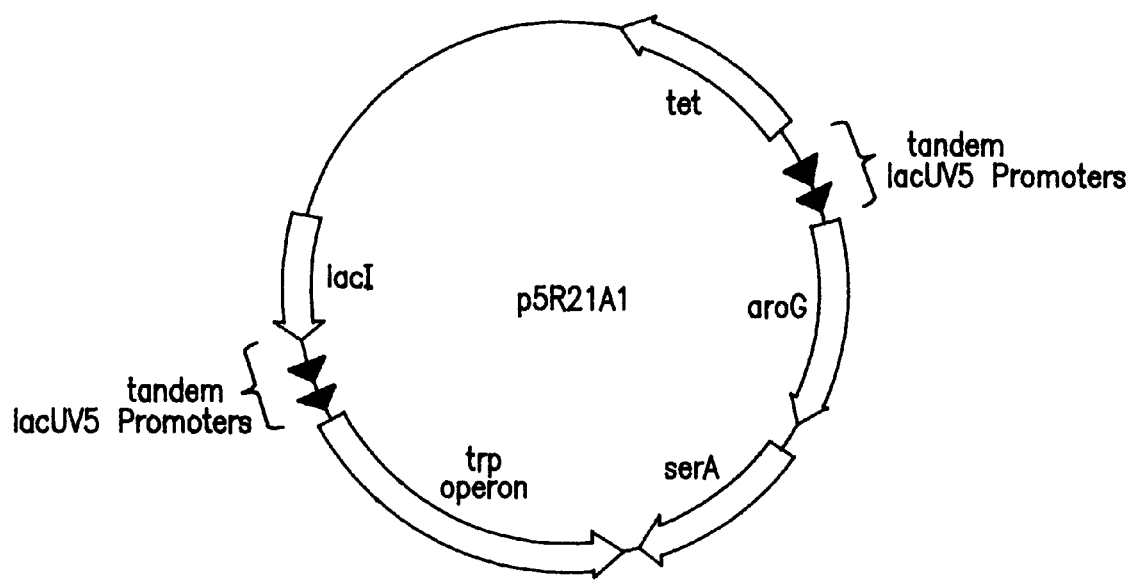

A similar set of plasmids with the tac promoter controlling the trp operon and tandem lacUV5 promoters controlling the aroG gene has also been constructed. Plasmid p5P11 A1 is one of this set and is shown in FIG. 10. Plasmids have also been constructed with tandem lacUV5 promoters controlling both the trp operon and the aroG gene. Plasmid p5R21A1 is one of this set and is shown in FIG. 10. These plasmids described in this section were transformed into the host strain JB102 in order to measure tryptophan synthesis.

4. Tryptophan production.

The original tryptophan producer JB102/pBE7 is compared with the various tryptophan plasmids constructed in this work. Initially, each strain is cultured with shaking in 20 mls of seed medium (28 g/l glucose, 24 g/l $K_2HPO_4$, 10 g/l $KH_2PO_4$, 5 g/l $(NH_4)_2SO_4$, 1 g/l $MgSO_4.7H_2O$, pH 7.2) at 37° C. for 24 hrs. Then 5 mls of the seed medium is inoculated into 20 mls of fermentation medium (35 g/l glucose, 2 g/l $MgSO_4.7H_2O$, 2 g/l citric acid, 25 g/l $(NH_4)_2SO_4$, 7.5 g/l $KH_2PO_4$, 20 g/l $CaCO_3$, 1 g/l $Na_2SO_4$, 0.2 g/l $MnSO_4$, 0.2 g/l $ZnCl_2$, 0.2 g/l $CoCl_2.6H_2O$, 0.03 g/l $CuSO_4.5H_2O$, 3.75 g/l $FeSO_4.7H_2O$, pH 7.2) and shaken at 37° C. for 24 hr. The amount of tryptophan in the fermentation medium is then determined by high pressure liquid chromatography (HPLC).

Some fermentations used the lactose analog, isopropyl-β-D-thiogalactoside (IPTG) to measure its effect. IPTG is an inducer of the lacI gene, which in turn can induce or up-regulate the tac promoter.

The results are shown in Table 1. It is believed from these results that the promoters and genes used in the present invention may already be optimally producing gene products used for tryptophan production and that other factors form the bottleneck for increased tryptophan production. Thus, the addition of IPTG or other lactose analogs to fermentations does not appear necessary for increased tryptophan production.

TABLE 1

|  | tryptophan g/l (−IPTG) | tryptophan g/l (+IPTG) |
| --- | --- | --- |
| JB102/pBE7 | 0.61 | 1.97 |
| JB102/p5R21 | 0.90 | 2.53 |
| JB102/p5P11A1 | 2.40 | 2.55 |
| JB102/p5LRPS2 | 3.03 | 2.98 |
| JB102/p5LRPS3 | 3.28 | 2.94 |
| JB102/p6LRPS2 | 2.89 | 2.96 |
| JB102/p6LRPS3 | 2.02 | 1.88 |

5. Tryptophan production in 5 L fermenters.

Larger scale fermentations were done to measure tryptophan production.

Batch fed fermentations were done in 5 liter vessels. There were three stage fermentations with a shake flask stage to start the bacterial strain's growth; a seed fermenter stage which is inoculated with material from the shake flask fermentation; and a main fermenter stage, inoculated with material from the seed fermenter. These fermentations were run at both high back pressure (15–17 lbs) and low back pressure (1–2 lbs) in the main fermenter stage.

The shake flask stage required that the strains be initially cultured at 37° C. in a shake flask medium (9.5 g/l $KH_2PO_4$, 24.4 g/l $K_2HPO_4$, 15 g/l yeast extract, 5.0 g/l $(NH_4)_2SO_4$, 32.6 g/l glucose, 1 g/l $MgSO_4.7H_2O$, 50 mg/l tetracycline). After about 12 hrs of growth at 37° C., an optical density at 660 nanometers (OD660) of 6–10 is reached.

The shake flask culture (0.65 mls) is then added to a volume of 2.1 liters in the seed fermenter stage. The seed fermenter medium contains: 1 g/l yeast extract, 1.2 g/l $(NH_4)_2SO_4$, 5.6 g/l $KH_2PO_4$, 1.6 g/l $MgSO_4.7H_2O$, 1.6 g/l Na citrate, 50 g/l glucose, 1.2 mg/l thiamine, 3 mg/l $MnSO_4.H_2O$, 15 mg/l $FeSO_4.7H_2O$, 0.7 mg/l biotin, pH 7. These fermenter cultures are grown about 12 hrs to an OD660 of approximately 8.

Main fermenters, having 2.1 liters of media, are inoculated with 175 mls of seed culture. The main fermenter medium is: 2.2 g/l $(NH_4)SO_4$, 10.5 g/l $KH_2PO_4$, 2.8 g/l citric acid, 2.8 g/l MgSO$_4$.7H$_2$O, 28 mg/l Na$_2$SO$_4$, 6.3 mg/l MnSO$_4$.H$_2$O, 7.4 mg/l ZnSO$_4$.H$_2$O, 5.6 mg/l CoCl$_2$.6H$_2$O, 0.8 mg/l CuSO$_4$.5H$_2$O, 0.1 g/l FeSO$_4$.7H$_2$O, 5 g/l glucose, pH 6.5. The main fermenters were run at both high (15–17 lbs) and low (1–2 lbs) back pressures. The high pressure fermenters were maintained at 10% dissolved oxygen (D.O.) and the low pressure fermenters were maintained at 20% D.O. The high pressure runs also used NH$_3$ gas for maintaining pH 6.5 and the low pressure runs used NH$_4$OH for maintaining pH 6.5. Agitation was used to maintain the proper D.O. levels. When the initial glucose is depleted, the fermentation is fed glucose to maintain a glucose concentration of less than 0.1 g/l according to the following typical feed schedule:

| Time  | g/l/hr |
|-------|--------|
| 0 hr  | 1.77   |
| 1 hr  | 3.68   |
| 2 hr  | 5.60   |
| 3 hr  | 7.37   |
| 4 hr  | 9.13   |
| 5 hr  | 11.29  |
| 6 hr  | 12.97  |
| 7 hr  | 14.74  |
| 8 hr  | 17.14  |
| 20 hr | 14.74  |
| 26 hr | 11.29  |

The fermentations were generally run for 51 hrs at 35° C. Table 2 shows the comparison of the high and low pressure tryptophan production data.

TABLE 2

|  | low pressure | | high pressure | |
|---|---|---|---|---|
|  | g of trp/fermenter | yield | g of trp/fermenter | yield |
| JB102/pBE7 | 133 | 11.2% | 122 | 9.8% |
| JB102/p5P11A1 | 152 | 12% | 149 | 12.5% |
| JB102/p5LRPS2 | 156 | 12.8% | 165 | 13.8% |

The inventive strains are easier to handle in the fermentation than the original strain, JB102/pBE7, and make more tryptophan than JB102/pBE7 in both the high and low back pressure conditions. The data are reported as grams of tryptophan per fermenter because the aqueous NH$_3$OH used to control the pH in the low pressure runs increases the total volume in the fermenters by as much as 10% more than the high pressure fermentations where NH$_3$ gas is used to control pH. The yield of tryptophan from glucose (g tryptophan produced/g glucose consumed) also gives an indication of the relative efficiency of the different strains. The starting strain, JB102/pBE7, has a lower yield at high back pressure than at low back pressure but, unexpectedly, the two inventive strains tested, JB102/p5P11A1 and JB102/p5LRPS2, perform better at high back pressure than at low back pressure. Interestingly, JB102/p5LRPS3 appears to perform less well in fermenters than these two strains. It is believed that increasing the back pressure in a lab scale fermenter will result in a better model of production scale fermentations.

Those who are skilled in the art will readily perceive how to modify the invention. Therefore, the appended claims are to be construed to cover all equivalent structures which fall within the true scope and spirit of the invention.

We claim:

1. A bacterium which comprises a host of the species *Escherichia coli* and a plasmid with the pBR322 origin of replication carrying genes from *Escherichia coli* for trpEDCBA, aroG, serA and lacl.

2. The bacterium of claim 1 where the trpEDCBA and aroG gene of the plasmid are controlled by a first and second lac promoter and a lacI gene product.

3. The bacterium of claim 1 where said plasmid has the trpEDCBA and aroG genes controlled by a first and second tac promoter and a lacI gene.

4. A bacterium containing a plasmid selected from the group consisting of p5LRPS2, p5LRPS3, p6LRPS2, p6LRPS3, p5P11A1, p5R21A1 or any combination of said plasmids with tandem lacUV5 promoters or tac promoters controlling a gene selected from the group consisting of trpEDCBA and aroG.

5. The bacterium of claim 4 wherein the bacterium is JB102.

6. The bacterium of claim 4 wherein the plasmid is p5LRPS2.

7. A method of producing tryptophan comprising the steps of culturing the bacterium in claim 1 in medium for a period of time sufficient for said bacterium to produce tryptophan, and removing said tryptophan from the culture medium.

8. A method of producing tryptophan comprising the steps of culturing the bacterium in claim 2 in medium for a period of time sufficient for said bacterium to produce tryptophan, and removing said tryptophan from the culture medium.

9. A method of producing tryptophan comprising the steps of culturing the bacterium in claim 3 in medium for a period of time sufficient for said bacterium to produce tryptophan, and removing said tryptophan form the culture medium.

10. A method of producing tryptophan comprising the steps of culturing the bacterium in claim 4 in medium for a period of time sufficient for said bacterium to produce tryptophan, and removing said tryptophan form the culture medium.

11. A method of producing tryptophan comprising the steps of culturing a bacterium JB102(p5LRPS2) in medium under high back pressure for a period of time sufficient for said bacterium to produce tryptophan, and removing said tryptophan from the culture medium.

* * * * *